US00PP35076P2

(12) United States Plant Patent
Uría

(10) Patent No.: US PP35,076 P2
(45) Date of Patent: Mar. 28, 2023

(54) ***SALVIA* PLANT NAMED 'ARGGR17011'**

(50) Latin Name: ***Salvia guaranitica* x *Salvia orbignaei***
Varietal Denomination: ARGGR17011

(71) Applicant: Rolando Aníbal Uría, Mar del Plata (AR)

(72) Inventor: Rolando Aníbal Uría, Mar del Plata (AR)

( * ) Notice: Subject to any disclaimer, the term of this patent is extended or adjusted under 35 U.S.C. 154(b) by 0 days.

(21) Appl. No.: 17/887,391

(22) Filed: Aug. 12, 2022

(30) Foreign Application Priority Data

Jan. 18, 2022 (QZ) ..... PBR 20220165

(51) Int. Cl.
*A01H 5/02* (2018.01)
*A01H 6/50* (2018.01)

(52) U.S. Cl.
USPC ..... Plt./475
CPC ..... *A01H 6/508* (2018.05); *A01H 6/50* (2018.05)

(58) Field of Classification Search
USPC ..... Plt./475
CPC ..... A01H 5/02
See application file for complete search history.

*Primary Examiner* — Kent L Bell
(74) *Attorney, Agent, or Firm* — Penny J Aguirre

(57) ABSTRACT

A new cultivar of hybrid *Salvia* plant named 'ARGGR17011' that is characterized by its bushy upright plant habit, its leaves that are small in size, its flowers that are pink in color, its foliage that is pale green in color, and its clump-forming growth habit with short, spreading rhizomes.

2 Drawing Sheets

Botanical classification: *Salvia guaranitica* x *Salvia orbignaei.*
Variety denomination: 'ARGGR17011'.

BACKGROUND OF THE INVENTION

The present invention relates to a new and distinct cultivar of *Salvia* plant, botanically of hybrid origin and known as *Salvia* 'ARGGR17011' and will be referred to hereinafter by its cultivar name, 'ARGGR17011'. 'ARGGR17011' is an herbaceous perennial grown for landscape use and for use as a container plant.

The new invention arose from an ongoing controlled breeding program in Mar del Plata, Argentina. The goal of the breeding program was to develop a new cultivar of *Salvia* with a bushy upright plant habit, smaller leaves, pink flowers and pale green foliage.

The Inventor made a controlled cross in March of 2016 in Mar del Plata, Argentina between *Salvia guaranitica* 'Amistad' (U.S. Plant Pat. No. 23,578) as the female parent and an unnamed and unpatented plant of *Salvia orbignaei* as the male parent. 'ARGGR17011' was selected in March of 2017 as a single unique plant amongst the resulting seedlings.

Asexual propagation of the new cultivar was first accomplished by softwood stem cuttings in Mar del Plata, Argentina in March 2017 under the direction the Inventor. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'ARGGR17011' as a unique cultivar of *Salvia.*

1. 'ARGGR17011' exhibits a bushy upright plant habit.
2. 'ARGGR17011' exhibits leaves that are small in size.
3. 'ARGGR17011' exhibits flowers that are pink in color.
4. 'ARGGR17011' exhibits foliage that is pale green in color.
5. 'ARGGR17011' exhibits clump-forming growth habit with short, spreading rhizomes.

The female parent of 'ARGGR17011' differs from 'ARGGR17011' in having a taller and less compact plant habit, flowers that are blue to mauve in color, and foliage that is dark green in color. The male parent of 'ARGGR17011' differs from 'ARGGR17011' in having woody stems (not herbaceous), inflorescences with flowers that are less congested, and leaves that are more narrow. 'ARGGR17011' can be compared to the *Salvia* cultivars 'Amante' (U.S. Plant Pat. No. 31,104) and 'Black and Bloom' (U.S. Plant Pat. No. 27,183). 'Amante' differs from 'ARGGR17011' in having a non-spreading plant habit, calyxes that are almost black in color, and flowers that are fuchsia to red in color. 'Black and Bloom' differs from 'ARGGR17011' in having a non-spreading plant habit, calyxes that are almost black in color, and flowers that are blue in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Publications include website listings by Crocus co., Thompson & Morgan, Plantagogo, Hayloft Plants, Middleton Nurseries, Van Meuwen, Cowell's Garden Center, Western Salvias, Economy and Viveros, National Gardening Association, Coolings Co, Scog (Twitter), Hardys Cottage Garden Plants, Barnes Nurseries, Vitroflora, Knight Garden Centers, The English Garden Co., Genesis Marketing Co., RHS Plants, Chelsea Flower Show, Camolin Potting Shed, Dobies Co., JP Parkers, and Le Chatel des vivaces.

BRIEF DESCRIPTION OF THE DRAWINGS

The accompanying color photographs illustrate the overall appearance and distinct characteristics of a 6-month-old plant of the new *Salvia* as grown outdoors in a 17-cm container in Lisse, The Netherlands.

The photograph in FIG. 1 provides a side view of 'ARGGR17011' in bloom.

Figure 1:
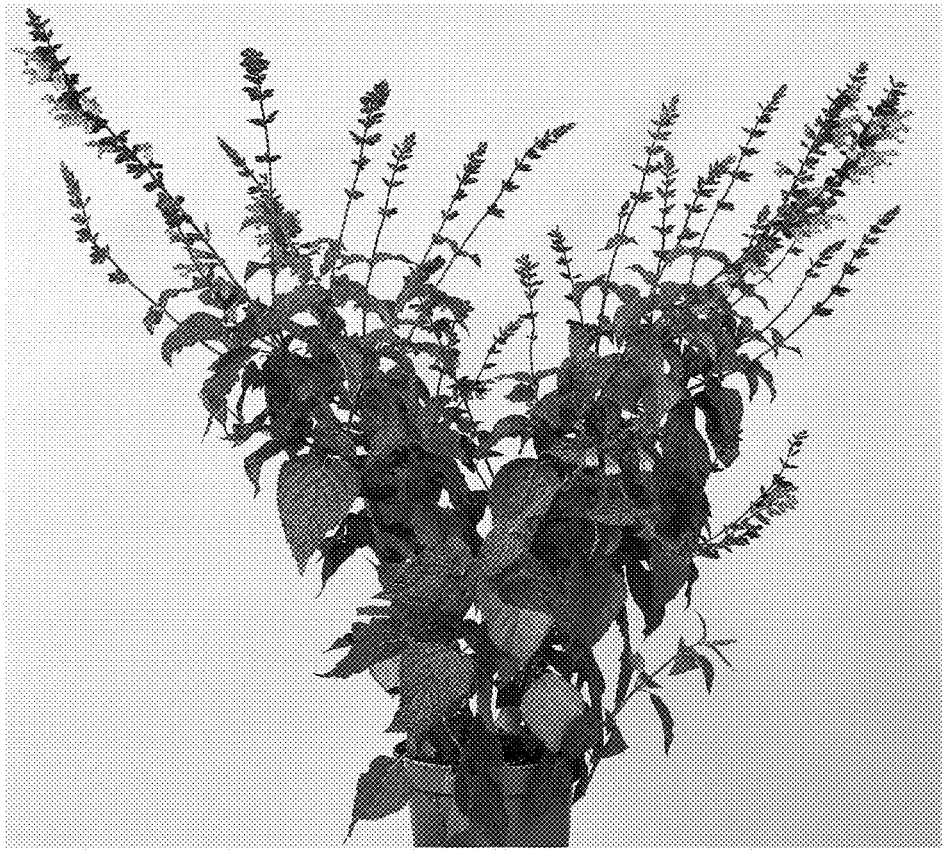
Figure 2:
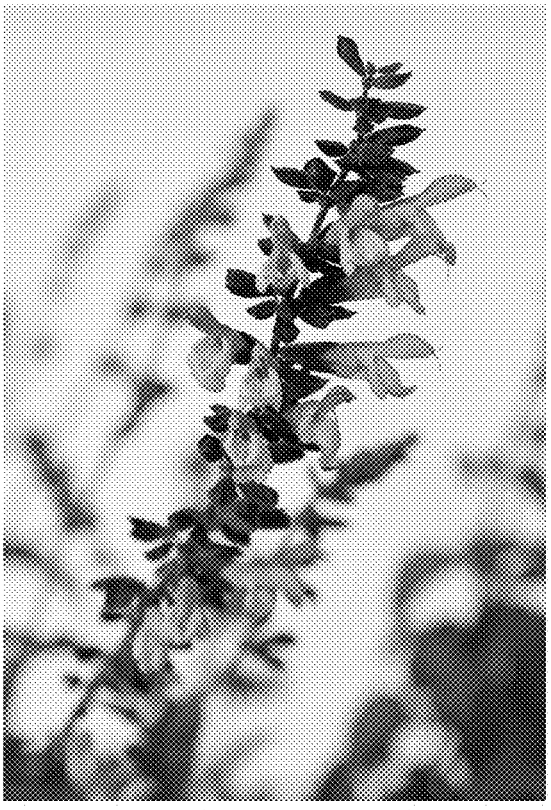

The photograph in FIG. 2 provides a close-up view of a flowering stem of 'ARGGR17011'.

Figure 3:
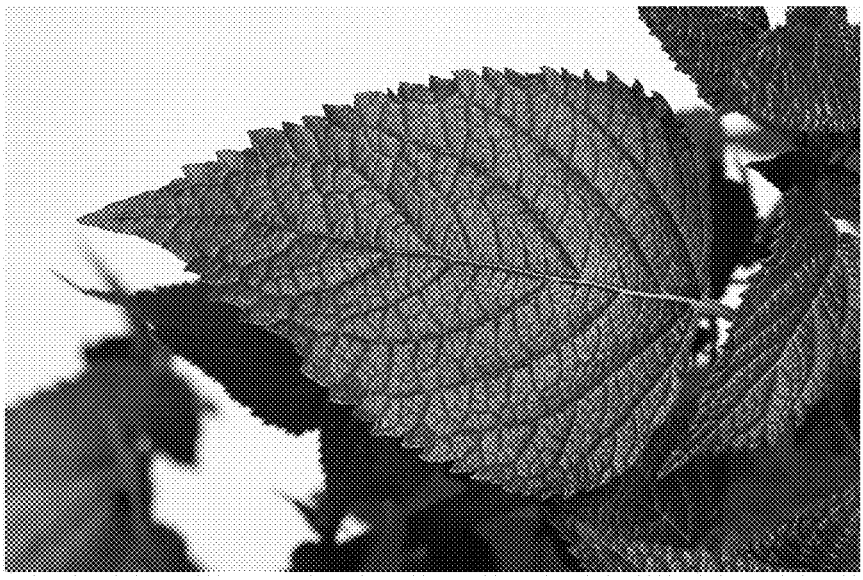

The photograph in FIG. 3 provides a close-up view of the foliage of 'ARGGR17011'.

The colors in the photographs may differ slightly from the color values cited in the detailed botanical description, which accurately describe the colors of the new *Salvia*.

DETAILED BOTANICAL DESCRIPTION

The following is a detailed description of the new cultivar of 6-month-old plants as grown outdoors in 17-cm containers in Lisse, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—May to October in the Netherlands.

*Plant type.*—Herbaceous perennial.

*Plant habit.*—Bushy, upright, spreading with short rhizomes.

*Plant size.*—An average of 51 cm in height (soil level to top of floral plane), 70 cm in height (soil level to top of floral plane) and 110 cm in spread as a 6-month old plant.

*Hardiness.*—At least in U.S.D.A. Zones 8 to 10.

*Diseases and pests.*—No susceptibility or resistance to diseases or pests has been observed.

*Root description.*—Fibrous on short rhizomes.

*Propagation.*—Softwood stem cuttings.

*Growth rate.*—Moderately vigorous.

*Root development.*—2 weeks for root initiation and about 4 weeks to produce a fully young plant.

Stem description:

*Shape.*—Quadrangular.

*Stem color.*—New growth; 143B, mature stems; 144A, single axillary stripe 147A.

*Stem size.*—Average of 52 cm in length (excluding inflorescence), 8 mm in diameter.

*Stem surface.*—Moderately glossy, moderately covered with short hairs, average of 1.5 mm in length, transparent and NN155D in color.

*Stem aspect.*—Average of 65°.

*Stem strength.*—Strong.

*Internode length.*—Average of 5.8 cm.

*Branching.*—Average of 2 primary branches, 9 secondary branches.

Foliage description:

*Leaf shape.*—Broadly ovate.

*Leaf division.*—Simple.

*Leaf base.*—Truncate.

*Leaf apex.*—Acute.

*Leaf venation.*—Pinnate, 146D in color on upper surface, 145A in color on lower surface.

*Leaf margins.*—Serrate.

*Leaf arrangement.*—Opposite.

*Leaf attachment.*—Petiolate.

*Leaf surface.*—Upper surface moderately glossy, and moderately covered with very short hairs, average of 0.3 mm in length, too small to measure color, lower surface matte, both sides rugose, moderately covered with very short hairs; 0.2 mm in length, too small to measure color.

*Leaf size.*—Up to 11 cm in length and 7.3 cm in width.

*Leaf color.*—Young upper surface 139A, young lower surface 147B, mature upper surface NN137A and 147A, mature lower surface 147B.

*Petioles.*—Average of 3.9 cm in length, 2 mm in width at widest point, strong, color; upper surface 148C, margins 148A, lower surface 143C and 144B, upper surface slightly glossy, lower surface matte.

Inflorescence description:

*Inflorescence type.*—Terminal verticillaster.

*Lastingness of inflorescence.*—Individual flowers average of 10 days, very freely flowering, self-cleaning.

*Inflorescence size.*—An average of 38.8 cm in height and 7.6 cm in width.

*Flower type.*—Single, labiate.

*Flower number.*—An average of 112 flowers per inflorescence, quantity of flowers and buds per plant 3,000.

*Flower aspect.*—Outward.

*Flower fragrance.*—None.

*Flower buds.*—Oblanceolate to narrow obovate in shape, average of 1.8 cm in length and 5.5 mm in diameter, color; 61A, immature sepals 146A, top a blend of 200A and 203B, base 143B, surface is matte and moderately pubescent with short glandular hairs; average of 0.5 mm in length, too small to measure color.

*Flower size.*—1.1 cm in diameter (horizontal), 1.5 cm in diameter (vertical), depth 4.4 cm, throat diameter 3 mm, tube 2.5 cm in length and 9 mm in diameter.

*Peduncle* (*Rachis*).—Quadrangulate, an average of 38.2 cm in length and 3 mm in width, held in an average angle of 35°, color 146D, tinged N186C, strong, surface is slightly glossy, moderately covered with very short hairs; 0.75 mm in length, N155A in color.

*Pedicels.*—An average of 6 mm in length and 1 mm in width, held in an average angle of 30°, 148A in color, moderately strong, surface is matte and densely covered with very short hairs; 0.2 mm in length, too small to measure color.

*Calyx.*—Campanulate, about 1.6 cm in length and 6 mm in diameter.

*Sepals.*—2, oblanceolate in shape, fused, 1.6 cm in length, 7 mm in width, apex acute, tip of sepal cleft, upper surface smooth, glabrous, matte, lower surface matte and moderately covered with very short glandular hairs, 0.5 mm in length and too small to measure color, color: upper surface when opening and fully open 146B to 146D, tinged at the top a blend of 147A and 200A, lower surface when opening and fully open; 146A, tinged towards the top a blend of 200A and 203B, immature sepals 143B.

*Petals.*—Labiate, 1 upper lip, 1 lower lip, average of 2 per flower, 1 whorl, lower 50% fused, color: when opening and fully open upper surface; upper lip 70B, lower lip 72C, when opening and fully open lower surface; 71D, throat color; 75A, tube color; 70B, upper lip; 4 mm in length, 4 mm in width, obovate in shape and folded, emarginate tip, fused into tube, entire, non-undulate, upper surface glabrous, slightly velvety, very slightly glossy, lower surface very slightly velvety, moderately covered with pubescent, short glandular hairs, 0.3 mm in length, 64A in color, lower lip; 3.5 cm in length, 1.1 cm in width, broadly obovate in shape with a single obovate lobe on each side, emarginate tip, fused into tube, entire, medium undulate, upper surface glabrous, slightly velvety, very slightly glossy, lower surface very slightly velvety.

Reproductive organs:

*Gynoecium.*—Pistil; 1, average of 4.4 cm in length, style; 8 mm in length, 73C, base 155A, stigma; 4 mm in diameter, cleft, decurrent in shape, 77A in color, ovary; 151D in color.

*Androecium.*—Stamens; 2, filaments; 75B in color, average of 1.4 cm in length, anthers; narrow oblong, dorsifixed, 5 mm in length, 0.75 mm in width, 177D, pollen; low, 159D in color.

*Fruit and seed.*—None observed to date.

It is claimed:

1. A new and distinct cultivar of *Salvia* plant named 'ARGGR17011' as herein illustrated and described.

* * * * *